(12) United States Patent
Sutherland et al.

(10) Patent No.: US 11,696,726 B2
(45) Date of Patent: Jul. 11, 2023

(54) ADHERENCE MONITOR FOR A MEDICAMENT INHALER WITH TETHERED CAP

(71) Applicant: ADHERIUM (NZ) LIMITED, Auckland (NZ)

(72) Inventors: Garth Campbell Sutherland, Auckland (NZ); Michael James Gormack, Auckland (NZ); Benjamin Laurence Wilson, Auckland (NZ); Tony Paul Kirker, Auckland (NZ); Hein Beyleveld, Auckland (NZ); Benjamin Lance Catt, Auckland (NZ)

(73) Assignee: Adherium (NZ) Limited

( * ) Notice: Subject to any disclaimer, the term of this patent is extended or adjusted under 35 U.S.C. 154(b) by 847 days.

(21) Appl. No.: 15/998,971

(22) PCT Filed: Feb. 17, 2017

(86) PCT No.: PCT/IB2017/050893
§ 371 (c)(1),
(2) Date: Aug. 17, 2018

(87) PCT Pub. No.: WO2017/141194
PCT Pub. Date: Aug. 24, 2017

(65) Prior Publication Data
US 2021/0204870 A1     Jul. 8, 2021

(30) Foreign Application Priority Data

Feb. 17, 2016 (AU) .............................. 2016900558

(51) Int. Cl.
*A61M 15/00* (2006.01)
*A61B 5/00* (2006.01)
*G16H 20/13* (2018.01)

(52) U.S. Cl.
CPC ......... *A61B 5/4833* (2013.01); *A61M 15/007* (2014.02); *A61M 15/0026* (2014.02);
(Continued)

(58) Field of Classification Search
CPC .. A61B 5/4833; A61M 15/0021–0026; A61M 15/007; A61M 15/0083;
(Continued)

(56) References Cited

U.S. PATENT DOCUMENTS 3,789,843 A * 2/1974 Armstrong ........ A61M 15/0091
128/200.23
5,165,391 A * 11/1992 Chiesi ............... A61M 15/0086
128/200.14
(Continued)

FOREIGN PATENT DOCUMENTS

WO   WO2005/046774 A1   5/2005
WO   WO2011/083377 A1   7/2011
WO   WO2015/030610 A2   3/2015

OTHER PUBLICATIONS

International Search Report and Written Opinion for PCT Patent App. No. PCT/IB2017/050893 (dated May 10, 2017).

*Primary Examiner* — Justine R Yu
*Assistant Examiner* — Alexander Morales
(74) *Attorney, Agent, or Firm* — Heisler & Associates (57) ABSTRACT

Some embodiments are directed to an adherence monitor for use with a tethered cap inhaler device. The adherence monitor engages the inhaler device, and includes a tether opening located within a housing of the adherence monitor for receiving the tether. The tether opening is in the form of a slot in a base portion of the housing. The path length of the tether around the adherence monitor is kept from being increased, compared to its path length when the adherence monitor is not attached to the inhaler, by having the slot located to allow the tether to pass through the slot. Various sensors of the adherence monitor in various embodiments detect inhaler usage.

20 Claims, 5 Drawing Sheets

(52) U.S. Cl.
CPC ........ *A61M 15/0083* (2014.02); *G16H 20/13* (2018.01); *A61M 15/009* (2013.01); *A61M 2205/14* (2013.01); *A61M 2205/18* (2013.01); *A61M 2205/332* (2013.01); *A61M 2205/3306* (2013.01); *A61M 2205/3331* (2013.01); *A61M 2205/3375* (2013.01); *A61M 2205/502* (2013.01); *A61M 2205/52* (2013.01); *A61M 2205/581* (2013.01); *A61M 2205/582* (2013.01); *A61M 2205/583* (2013.01); *A61M 2205/587* (2013.01); *A61M 2205/8206* (2013.01)

(58) Field of Classification Search
CPC ............ A61M 15/009; A61M 2205/14; A61M 2205/18; A61M 2205/3306; A61M 2205/332; A61M 2205/3331; A61M 2205/3375; A61M 2205/502; A61M 2205/52; A61M 2205/581; A61M 2205/582; A61M 2205/583; A61M 2205/587; A61M 2205/8206; G16H 20/13
USPC ........................ 128/200.14, 200.17
See application file for complete search history.

(56) References Cited

U.S. PATENT DOCUMENTS

| | | | |
|---|---|---|---|
| 5,730,118 A * | 3/1998 | Hermanson | A61M 15/00 128/200.14 |
| 6,202,642 B1 * | 3/2001 | McKinnon | A61M 15/0083 128/200.14 |
| 7,552,728 B2 * | 6/2009 | Bonney | A61M 15/0081 128/207.14 |
| 8,225,790 B2 * | 7/2012 | Bowman | A61M 15/0091 239/338 |
| 8,251,056 B2 * | 8/2012 | Pearson | A61M 15/0081 128/200.14 |
| 2003/0163099 A1 * | 8/2003 | Wermeling | A61M 15/0081 604/275 |
| 2007/0023034 A1 | 2/2007 | Jongejan et al. | |
| 2007/0084462 A1 * | 4/2007 | Allen | A61M 15/008 128/200.23 |
| 2007/0186923 A1 * | 8/2007 | Poutiatine | A61M 15/0083 128/200.14 |
| 2008/0060642 A1 * | 3/2008 | Bunce | A61M 15/0065 128/200.23 |
| 2013/0269685 A1 * | 10/2013 | Wachtel | A61M 15/0065 128/200.14 |
| 2014/0000598 A1 * | 1/2014 | Sutherland | A61M 15/009 128/203.12 |
| 2014/0182584 A1 * | 7/2014 | Sutherland | A61M 15/0071 128/200.23 |
| 2014/0243750 A1 * | 8/2014 | Larsen | A61M 5/1452 604/189 |
| 2015/0066429 A1 * | 3/2015 | Nielsen | G16H 50/20 702/177 |
| 2016/0051776 A1 * | 2/2016 | Von Hollen | A61M 15/008 128/200.23 |
| 2016/0132660 A1 * | 5/2016 | Barajas | G06Q 10/10 705/2 |
| 2016/0144142 A1 * | 5/2016 | Baker | A61M 15/0021 128/200.23 |

* cited by examiner

ADHERENCE MONITOR FOR A MEDICAMENT INHALER WITH TETHERED CAP

CROSS REFERENCE TO RELATED APPLICATIONS

This application is a national phase filing under 35 C.F.R. § 371 of and claims priority to PCT Patent Application No. PCT/IB2017/050893, filed on Feb. 17, 2017, which claims the priority benefit under 35 U.S.C. § 119 of Australian Patent Application No. 2016900558, filed on Feb. 17, 2016, the contents of each of which are hereby incorporated in their entireties by reference.

BACKGROUND

Some embodiments relate to methods, devices and systems for monitoring adherence to medication regimes for inhalers with a tethered cap mouthpiece cover.

Some embodiments are directed to adherence monitors for pressurised metered dose inhalers (pMDI) with a tethered cap mouthpiece cover including, without limitation, pMDI fitted with a dose counter mechanism fitted onto the base of the medicament canister. These are often used in the treatment of respiratory diseases such as asthma, COPD, cystic fibrosis, and bronchiectasis. However, such devices may also be used to deliver other medications, for example for the treatment of pain, heart conditions, erectile dysfunction, diabetes, and other indications.

There are several different types of inhalers with tethered cap mouthpiece cover available on the market. In the USA, examples of the inhalers include: Ventolin™ HFA (GSK); Advair™ (GSK); Flovent™ (GSK); Duolin™ (Cipla); Symbicort™ (AstraZeneca) among others.

SUMMARY

A problem associated with the use of all medicament inhalers is poor adherence. Many studies have shown that users frequently do not take their medicament at the predetermined or prescribed times and/or in the required amounts. The consequences of this non-adherence can include minimized or reduced disease control, lower quality of life, lost productivity, hospitalisation and avoidable deaths. This represents a considerable cost to the users, as well as to the health system.

To address this problem, some of the inhalers incorporate dose counting mechanism to indicate the number of medicament doses delivered and/or the number of medicament doses remaining in the medicament inhaler. However, a limitation associated with early (mechanical) dose counters is that they were limited to just recording the number of doses only; that is, no other compliance data was gathered.

Adherence monitoring devices have been developed for use with medicament inhalers allowing for wider range of inhaler use data to be gathered and available to patients and healthcare providers.

Many inhalers include a cap over the mouthpiece. The cap ensures that the mouthpiece remains clean, and that no foreign objects can enter the mouthpiece. An issue associated with the use of all inhalers equipped with a cap is that users sometimes inadvertently administer medication (e.g. by pushing down the canister of a pMDI) without removing the cap from the inhaler. In such instance, an adherence monitoring device may still register a dose as delivered and not recognise that the canister actuation occurred when the cap was still on the mouthpiece.

The ability to record compliance data generally relating to when the cap is removed and replaced, and/or how many times the user dispenses (or attempts to dispense) a dose of medicament, with the cap still attached to the mouthpiece, would be very useful and important information, both for training purposes or feedback for the user, as well as for general medicament compliance data gathering purposes.

Patent application WO/2015/030610 by the present applicant discloses an adherence monitoring device for a medicament delivery device capable of detecting the presence or absence of a tethered cap on the mouthpiece and distinguishing between dose deliveries which occur with cap off, and unsuccessful attempts with cap on. In one embodiment, the presence or absence of cap is detected via a single switch located at the base of the adherence monitoring device.

While the above solutions have been effective in detecting cap removal and replacement, in the context of current and planned inhaler devices, the adherence monitors developed to date have several challenges:

(a) to releasably fit the adherence monitor onto the inhaler, the user has to first remove the inhaler cap, push the inhaler snugly into the adherence monitor and put the cap back on the mouthpiece;

(b) to fit the cap onto the mouthpiece, the user has to stretch the tether over the base of the adherence monitor and force the cap onto mouthpiece; and (c) the location of dose detection pressure sensor switch under the base of the inhaler exacerbates the problem of tether stretching.

In some pMDIs fitted with tethered caps, the tether is fitted more loosely and the base of the adherence monitor does not cause the tether to stretch. In other inhalers, for example, AstraZeneca's Symbicort™ pMDI, the tether fitting is tighter and therefore more likely to be affected by the base of an adherence monitor.

Some embodiments are therefore directed to an enhanced or an improved adherence monitor for inhalers equipped with a tethered cap.

In a first form, some embodiments are directed to an adherence monitor for an inhaler with a tethered cap, with an opening or slot in the device for the tether for the cap to pass through.

In a second form, some embodiments are directed to an adherence monitor for an inhaler with a moveable dose counter housing, in which a dose detection switch on the adherence monitor is positioned so as to be actuated by the movement of the dose counter housing.

In another form, some embodiments are directed to an adherence monitor configured to couple to an inhaler with a tethered cap, the adherence monitor adapted to detect a position of the tethered cap.

According to one aspect, some embodiments are directed to an adherence monitor for a medicament inhaler, the inhaler including a body, a mouthpiece for operatively inhaling the medicament, a cap for the mouthpiece, and a tether connecting the cap to the body, the adherence monitor including a tether opening for receiving the tether, so that the path length of the tether around the monitor is minimized or reduced.

The provision of the tether opening allows the user of the tethered pMDI to simply slide the inhaler into the adherence monitoring device, without the need to remove the cap prior to fitting the device one and without the need to stretch the tether to fit the cap back onto the mouthpiece. This provides significant advantages in the ease-of-use and ergonomics of the adherence monitor of some embodiments.

According to another aspect, some embodiments are directed to an adherence monitor for a medicament inhaler, wherein the tether opening is formed and positioned such that the tether may be inserted into or removed from the opening whilst the adherence monitor is operatively engaged with the inhaler.

According to another aspect, some embodiments are directed to an adherence monitor, wherein the adherence monitor may be fitted to the inhaler without removing the cap from the tether.

According to another aspect, some embodiments are directed to an adherence monitor, the adherence monitor further including a housing configured to enclose at least a portion of the medicament inhaler in use.

According to another aspect, some embodiments are directed to an adherence monitor, wherein the tether opening is a slot extending through a base portion of the housing, and the tether operatively passes through the slot, around the base to the mouthpiece.

According to another aspect, some embodiments are directed to an adherence monitor, wherein the housing includes at least one retainer configured to engage with a base portion of a medicament inhaler when the medicament inhaler is received within the housing.

According to another aspect, some embodiments are directed to an adherence monitor, the adherence monitor further including a cap detection system.

According to another aspect, some embodiments are directed to an adherence monitor, wherein the cap detection system is configured to detect a position of one or more of the cap or the tether of the inhaler when the inhaler is received within the adherence monitor.

According to another aspect, some embodiments are directed to an adherence monitor, wherein the cap detection system includes at least one sensor configured to detect a status of the cap, tether or cap and tether of the inhaler.

According to another aspect, some embodiments are directed to an adherence monitor, wherein the at least one sensor may include one or more of an acoustic sensor, vibrational sensor, pressure sensor, pressure switch, force sensor resistor, audible sensor, optical sensor or proximity sensor.

According to another aspect, some embodiments are directed to an adherence monitor, wherein the cap detection system is configured to detect a cap on status, the cap on status being when the cap of the inhaler is positioned on or over the mouthpiece of the inhaler.

According to another aspect, some embodiments are directed to an adherence monitor, wherein the cap detection system is configured to detect a cap off status, the cap off status being when the cap of the inhaler has been removed from or is not covering the mouthpiece of the inhaler.

According to another aspect, some embodiments are directed to an adherence monitor, the adherence monitor further including an alert system, the alert system configured to send a signal to the user following detection of a predetermined event.

According to another aspect, the predetermined event includes one or more of (i) the cap is removed from the mouthpiece of the inhaler; (ii) a dose of medicament has been administered (ii) time to take next dose of medication.

According to another aspect, the signal may be sent following expiry of a predetermined period of time following detection of the predetermined event.

According to another aspect, the alert system is activated when the cap has been removed for a predetermined period of time.

According to another aspect, the predetermined period of time is at least 1 second.

According to another aspect, the predetermined time is less than 60 minutes.

According to another aspect, the predetermined period of time is between 5 seconds and 30 minutes.

According to another aspect, the predetermined period of time is set by a user.

According to another aspect, some embodiments are directed to an adherence monitor for an inhaler, the inhaler including a moveable dose counter housing which moves when a dose of medicament is dispensed by the inhaler, the adherence monitor including a dose detection switch, wherein the dose detection switch is configured so that it is operatively actuated by the movement of the dose counter housing.

This arrangement allows for the effective detection of dose by an external monitor in this type of inhaler.

Advantageously, combining the tether opening and dose detection switch responsive to the movement of the dose counter housing provides a monitor which is easily fitted and used, and which accurately detects operation of the inhaler.

BRIEF DESCRIPTION OF THE FIGURES

An illustrative embodiment will be described with reference to the accompanying figures, in which.

DETAILED DESCRIPTION OF EXEMPLARY EMBODIMENTS

Throughout this specification, the terms "patient" or "user" or "person" or "patient usage", when used in relation to the use of a medicament delivery device, are to be understood to refer to any person that uses a medicament delivery device.

Exemplary embodiments will be described in relation to various specific implementations, which it will be understood are intended to be illustrative and not limitative of the scope of some embodiments. It will be appreciated in particular that various additional features and functions, indicators and the like may be included in monitors which implement some embodiments. These may be selected for specific application at the option of the product designer.

The following implementations will be described with reference primarily to pressurized metered dose inhalers (pMDI), as these are in widespread commercial use. However, some embodiments may, with suitable modifications as will be apparent to those of ordinary skill in the art, be applied to other designs of inhalers using tethered cap mouthpiece cover, presently known or yet to be developed.

Similarly, whilst the discussion below is principally in relation to respiratory related medicaments, it is applicable to any use of pMDI devices, including by way of example only pain medication, diabetes, erectile dysfunction, or other conditions. Some embodiments are directed to the monitoring of how the medication is used and dispensed, and should in no way be considered as limited to any particular medicament or condition.

As a general explanation, the implementations of an adherence monitor described are intended to be used with a medicament dispensing inhaler with a tethered cap or cover. The devices include systems to detect that a dose has been dispensed, and to retain or communicate a record of this to a remote system, for example via Bluetooth™ to a smartphone, tablet or other device. The intention is to automatically create a record of usage, to assist in clinical management. The devices may also provide reminders to the user, detect whether or not a dispensing device is attached, provide error indications, or provide other functions.

Some embodiments are directed to mechanical features and the location of switches in an adherence monitor. The electronics, communications, control software and the like may be in any suitable form, for example as is widely practiced and known in the art from the products available commercially from the applicant and related companies. Some embodiments do not impose any specific requirements in this regard. Reference should be had to, for example, the various references cited herein and incorporated by reference in order to provide further details of these aspects.

Figure 1A:
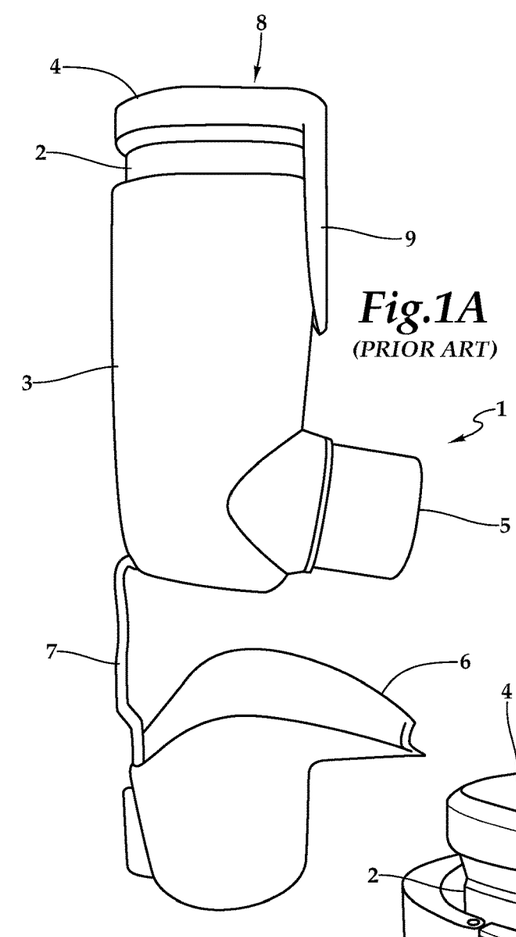
FIG. 1A is a side view of an exemplary related art pMDI with the tethered cap removed from the mouthpiece.
Figure 1B:
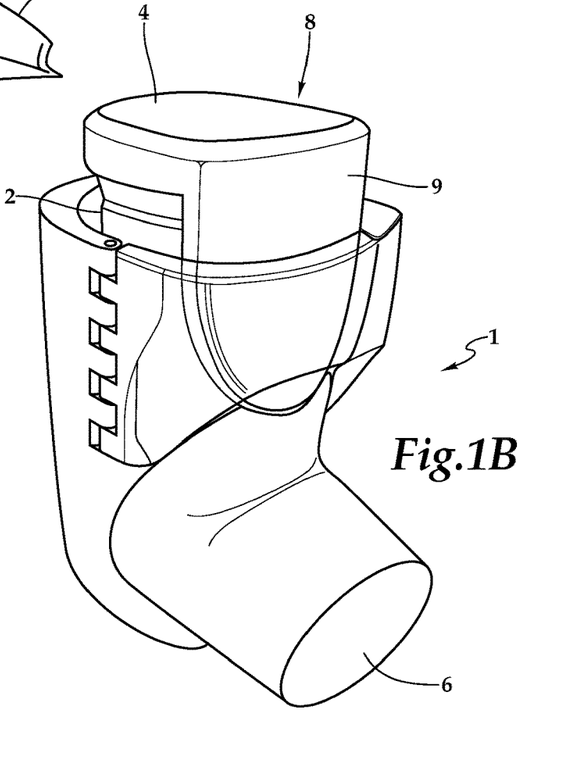
FIG. 1B is a perspective view of a first embodiment attached to the exemplary pMDI shown in FIG. 1A and cap on the mouthpiece.

FIG. 1A shows a related art pMDI medicament inhaler (Symbicort™ pMDI inhaler by AstraZeneca) device described in European Patent No. EP1875412. FIG. 1B shows the pMDI with an adherence monitor according to one implementation of some embodiments attached.

The medicament inhaler 1 includes a store of medicament in the form of a pressurised medicament canister 2, and an actuator 3 (for housing the canister 2). The medicament inhaler includes a dose counter 4 which when pressed down, pushes the canister 2 into actuation/firing position.

The inhaler 1 is also provided with a spray stem (not shown) extending from the canister 2, which is adapted to engage with a spray-directing element (not shown) housed within the actuator 3. When the canister 2 is pushed down into the actuator 3, the spray stem and spray-directing element combine to deliver a metered dose of medicament out through the mouthpiece 5 (not shown) of the actuator 3, and into the mouth of the user (who sucks on the mouthpiece 5 at the same time that the medicament is dispensed).

The inhaler 1 is also provided with a removable and replaceable cap 6, which is adapted to close off the mouthpiece 5 when the inhaler 1 is not in use. The cap 6 ensures that the mouthpiece 5 remains clean, and free from dust and grime, and also ensures that no foreign objects (such as coins) can enter the mouthpiece 5 (for example when the inhaler is not in use or being carried in a pocket or purse), which may otherwise present a choking hazard.

The cap 6 is attached to the rear of the actuator 3 by a tether 1. Having the cap 6 tethered to the actuator 3 in such a fashion ensures that the cap 6 is not inadvertently dropped or lost once it has been removed. Furthermore, having a tethered cap 6 ensures that the cap 6 does not become a choking hazard.

Some embodiments may be applied with any suitable type of tether. As will be understood by those of ordinary skill in the art, the details of the engagement between the tether and the cap will vary, and will be selected by the manufacturer. Suitable tethers may be made using flexible or rigid materials. Materials for a rigid plastic tether may include ABS, PP, LDPE, or Tritan. Materials for a flexible tether may include urethane or rubber.

The dose counter 4 includes a counter housing 8 and a counter mechanism (not shown). The housing 8, is provided with a shield-like downward-directed surface 9 the bottom edge of which abuts the top of the cap 6 when it is fitted onto the mouthpiece 5. When the cap 6 is on the mouthpiece 5, it blocks the movement of the housing 8, so that firing of the inhaler may be impossible.

Secondly, the downwards directed surface 9, is provided with an aperture (not shown) that is adapted to receive a protrusion (not shown) from the top edge (not shown) of the actuator body 3 in a mating relationship. When the housing 8 is depressed in order to actuate the inhaler device 1, the protrusion extends through the aperture into the counter housing 8 and actuates the counter mechanism.

The dose counter 4 is attached, advantageously or preferably permanently, to the canister 2, in order to avoid the removal of the counter 4 from one canister 2 and subsequent attachment of it onto another canister containing a different level of medicament. The canister 2 with the attached dose counter 4 unit 2 is hereafter referred to as an inhaler can assembly.

The adherence monitor 10 according to this implementation is housed within a second housing 11, which is releasably attachable to the inhaler 1 (or more specifically to the actuator 3).

Figure 2:
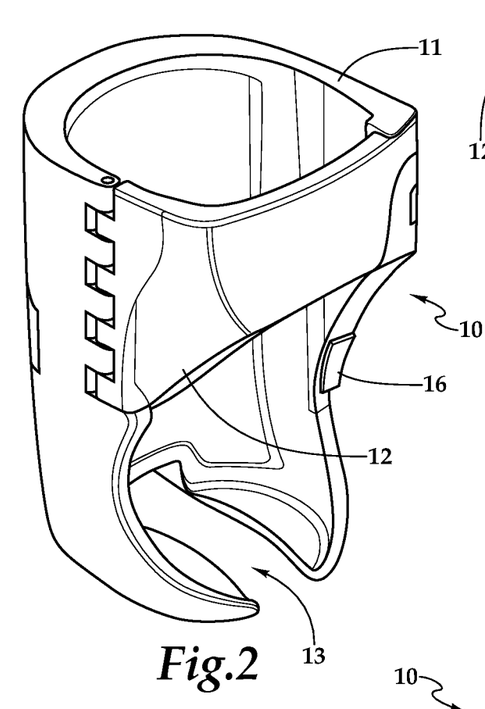
FIG. 2 is a perspective view of another embodiment, without the inhaler and with the hinged door of the adherence monitor closed.
Figure 3:
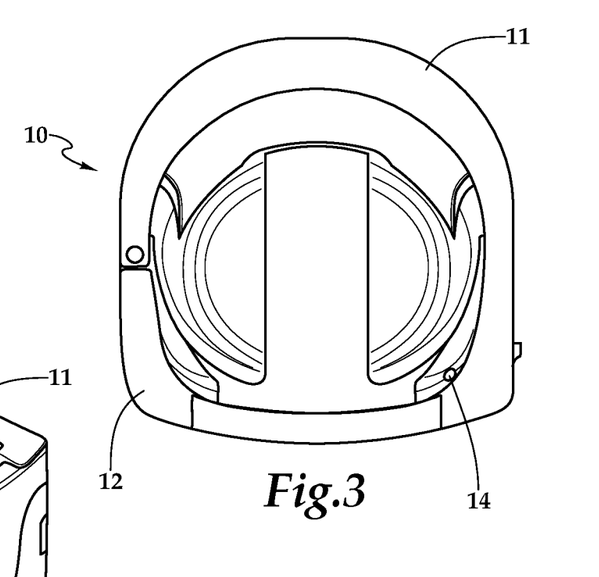
FIG. 3 is a top view of the embodiment illustrated in FIG. 2.
Figure 4:
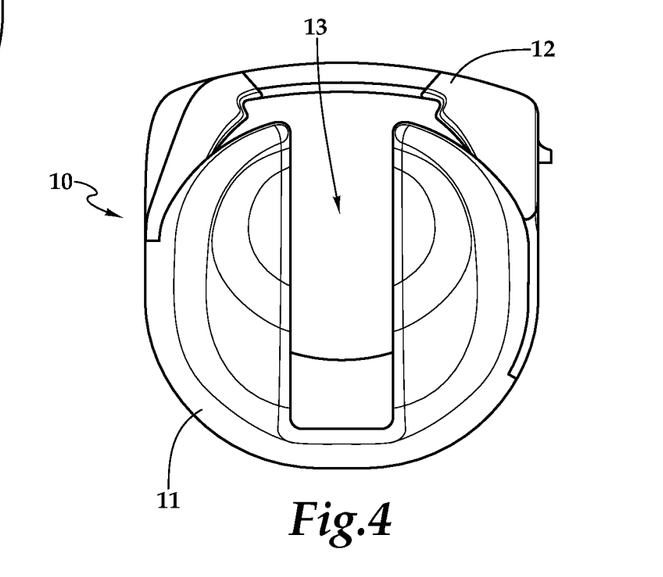
FIG. 4 is a bottom view of the embodiment illustrated in FIG. 2.

Referring to FIGS. 2-4, the second housing 11 is configured to only partially enclose the inhaler 1 when the inhaler is received in the adherence monitor 10. That is, the second housing 11 is configured to enclose the sides and front of the inhaler 1, and is fitted with a hinged door 12 which covers an opening at the front of the second housing 11. This opening allows for the inhaler 1 to be placed into, secured and/or removed from, the second housing 11. The hinged door is made with transparent plastics, to allow patients to refer to the medication label placed on the downward-directed surface 9 when the inhaler is positioned within the adherence monitor 10. As can be seen in FIG. 2, the opening at the front of the second housing 11 is between an interior of the housing where the body of the inhaler 1 is located and an exterior of the housing 11. The opening is seen in FIG. 2 to have a lateral border between sides of the housing 11 and the opening. This lateral border has a lower portion, extending further forward (from the interior through the opening) than a recessed portion of the lateral border located above the lower portion. A base portion of the housing 11 is seen in FIG. 2 to include a left floor portion and a right floor portion. These floor portions are located on opposite sides of the tether opening provided by the tether slot 13. These floor portions are shown in FIG. 2 to be bounded by a rear wall extending upwardly from rearward portions of the floor. The rear wall is positioned to resist rearward movement of the inhaler 1 relative to the floor of the base portion of the housing 11. The floor portions are shown in FIG. 2 to be bounded by side walls extending upwardly from lateral portions of the floor opposite the tether slot 13 and extending up to transition into becoming the sides of the housing 11. The side walls are positioned to resist lateral movement of the inhaler 1 relative to the floor of the base portion of the housing 11. The floor portions are shown in FIG. 2 to be bounded by front walls extending upwardly at least partially from forward portions of the floor. These front walls are positioned to resist forward movement of the medicament inhaler 1 relative to the floor of the base portion of the housing 11. These floor portions are shown in FIG. 2 to be bounded on inner sides thereof closest to each other by the slot 13 of the tether opening. The rear wall, lateral walls and front walls can be seen in FIG. 2 to act together to keep the inhaler 1 restrained when the inhaler 1 is inserted into the adherence monitor 10 and in contact with the floor, from any motion other than vertical motion of the canister 2 of the inhaler 1 relative to the actuator 3 of the inhaler 1, for dispensing of a dose of medicament out of the canister 2 and through the mouthpiece 5. Portions of the front walls above the floor portions can be seen in FIG. 2 to terminate below the cap 6 of the inhaler 1 when the cap 6 is located upon the mouthpiece 5 of the inhaler 1 and the inhaler 1 is located adjacent to the floor portions. This allows transitioning of the cap 6 from being on the mouthpiece 5 and off of the mouthpiece 5 to occur freely and fully without interference by the front walls, which extend upwardly at least partially from forward portions of the floor portions. As can be seen in FIGS. 1A and 1B, the opening in the front of the adherence monitor 10 and the lateral border of the opening of the adherence monitor 10 are positioned to avoid blocking the downward-directed surface 9 that is coupled to the canister 2 of the inhaler 1 and located on a front side of the inhaler 1. This keeps the inhaler 1 free from obstruction by the adherence monitor 10, whether the downward-directed surface 9 is in a first position or a second position that has moved downward relative to the first position when the cap 6 of the inhaler 1 is off of the mouthpiece 5 for actuation of the medicament inhaler 1 (see FIGS. 1A and 1B). As can be seen in FIGS. 1A, 1B and 2, the opening allows the cap 6 of the inhaler 1 to be placed on the mouthpiece 5 of the inhaler 1 to block downward movement of the downward-directed surface 9, and also allows actuation of the inhaler 1 without interference by the adherence monitor 10.

The adherence monitor 10 further includes a tether slot 13. The slot 13 allows for the inhaler 1 to be inserted into the adherence monitor 10 without the need for a prior removal of the cap 6, and without the need to stretch tether 7 over the base of the adherence monitor 10.

Figure 5:
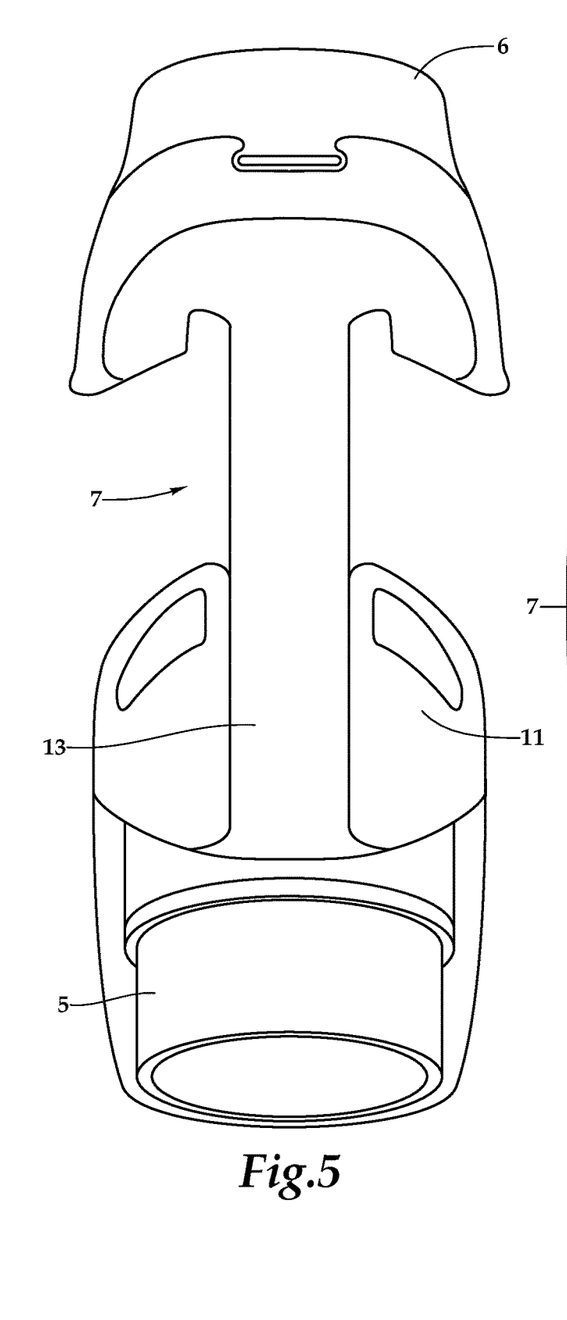
FIG. 5 is a bottom view of another embodiment attached to a pMDI with the tethered cap removed from the inhaler mouthpiece.
Figure 6:
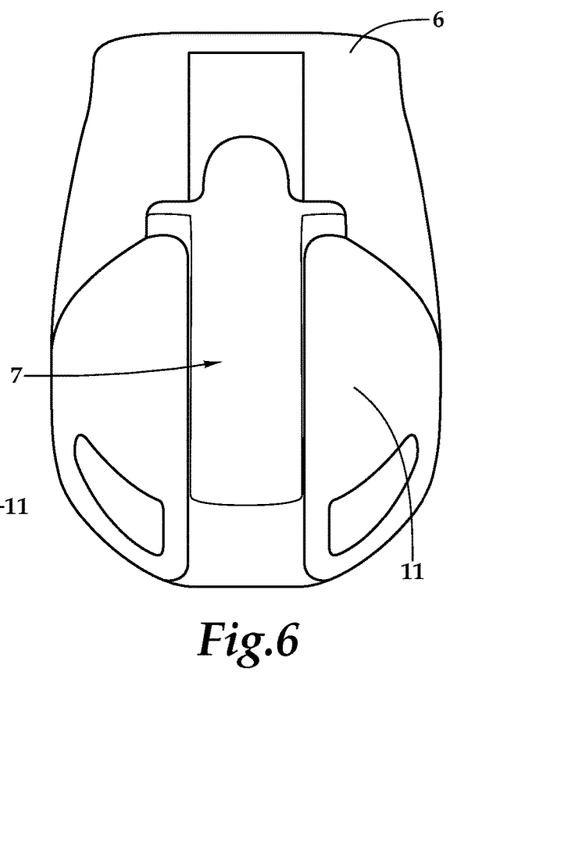
FIG. 6 is a bottom view of the embodiment illustrated in FIG. 5, with the adherence monitor attached to the inhaler and the mouthpiece covered by the tethered cap.

FIGS. 5 and 6 show bottom views of a pMDI inhaler positioned within an adherence monitor 10 according to an embodiment. FIG. 5 shows the cap 6 with the tether 7 disengaged or removed from the tethered slot 13 and mouthpiece 5. FIG. 6 shows the cap 6 positioned over or covering the mouthpiece 5 and the tether 7 located within the tether slot 13. The tether slot 13 acts to reduce or minimize the distance which the tether must or should cover to enable cap 6 to be attached to mouthpiece with the tether 7 remaining attached to the cap 6 and the actuator 3. The slot must or should be dimensioned so as to enable the free movement of the tether as required for attachment and removal of cap 6. The tethered slot 13 is advantageously or preferably provided in a base portion of the adherence monitor 10 that receives a base portion of the medicament inhaler.

In alternative arrangements, the adherence monitor 10 may include one or more retainers 15, 15' configured to engage within or couple to the base portion of the inhaler.

Figure 7:
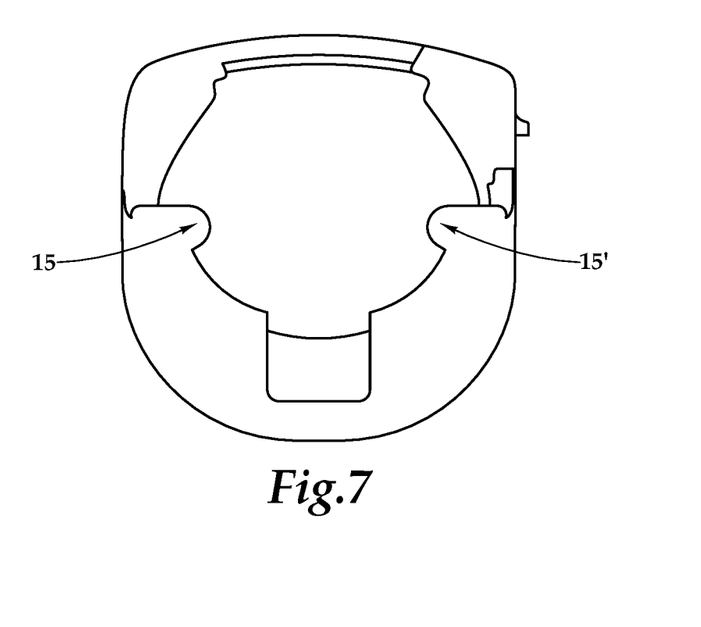
FIG. 7 is a bottom view of another embodiment.
Figure 8:
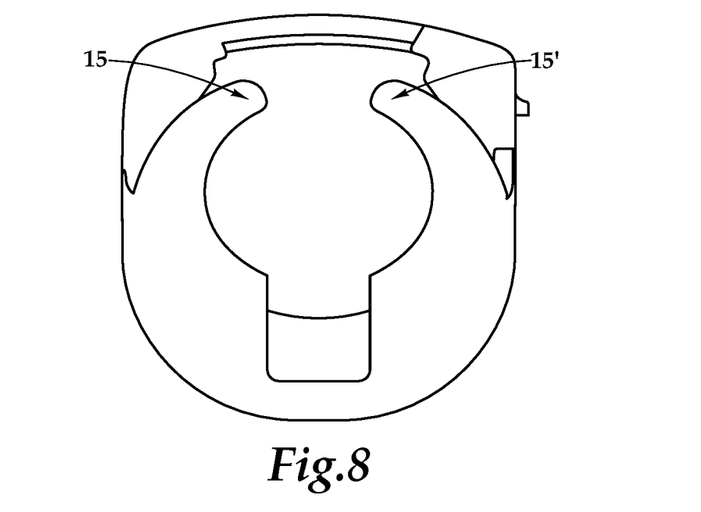
FIG. 8 is a bottom view of a further embodiment.

The one or more retainers 15, 15' are adapted to facilitate retention of the adherence monitor to the medicament inhaler 1, advantageously or preferably the base of the medicament inhaler 1, whilst enabling free movement of the tether 7 as required for removal and replacement/attachment of the cap 6. Thus, the one or more retainers are located adjacent to or surround the tether position of the inhaler 1, providing a tether opening to facilitate free movement of the tether 7. The one or more retainers may be in the form of claws, clasps, clamps, catches, clips, snaps or similar fasteners. Advantageously or preferably, there are at least two, three, four, five or more retainers located around the base of the adherence monitor 10. FIGS. 7 and 8 show two possible locations of such retainers, indicated with arrows 15 and 15'.

In some arrangements, the position or movement of the cap 6 or the tether 7 coupled to the cap 6 may be monitored or detected by the adherence monitor 10. In such arrangements, the adherence monitor 10 may detect a cap 'on' status, a cap 'off' status, both a cap 'on' and a cap 'off' status or movement or change in position of the tether 7 or the cap 6.

The cap 'on' status is said to occur when the cap 6 is covering or positioned over or on the mouthpiece 5. The cap 'off' status is said to occur when the cap 6 is off, i.e. not covering or not positioned on or over the mouthpiece 5. Each of the cap 'on' and cap 'off' status may be determined by detecting a position of the cap 6 or a position of the tether 7. The tether 7 will be in a first position when the cap 6 is positioned on or over the mouthpiece 5 and the tether 7 will be in a different position when the cap is off or not covering the mouthpiece 5.

In some forms the adherence monitor 10 may directly monitor: (a) when a cap is in the 'off' status; (b) when the cap is in the 'on' status; or (c) both the 'off' and 'on' status of the cap. If (a) or (b) are directly monitored, then the opposing status may be determined as occurring when the monitored status is not detected.

In some forms the adherence monitor 10 may detect whether the cap 6 is 'on' or 'off' using a sensor positioned on the adherence monitor 10. In some forms the sensor may be positioned on or adjacent the base of the adherence monitor 10. The sensor may be an infrared (IR) optical sensor or a proximity sensor or any other suitable sensor. For example, the sensor may include a sensor as described for use in the compliance monitor described in International Application number PCT/NZ2015/000037 published as WO 2015/174856 on 19 Nov. 2015, the contents of which is incorporated herein in its entirety.

The sensor may include an optical sensor including:

a) at least one light transmitter able to transmit an optical signal, b) at least one light receiver able to receive an optical signal, c) the arrangement and construction being such that movement of the cap 6 or the tether 7 (or both) alters the optical signal(s) whereby the optical sensor is able to determine the position of the cap.

Figure 9:
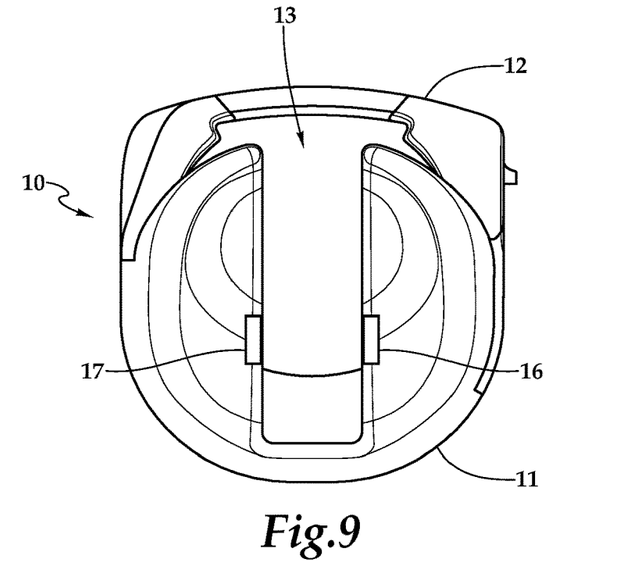
FIG. 9 is a bottom view of another embodiment.

In one embodiment, illustrated in FIG. 9, the light receiver(s) 16 may be positioned substantially opposite the light transmitter(s) 17 in order to receive a substantially direct beam of light, for example a laser beam. In such an embodiment, the position of the cap 6 or the tether 7 when the cap is in the 'on' position may block or partially block the beam of light, thus indicating the cap is 'on'. When the cap is removed to the 'off' position the cap 6 or tether 7 may no longer block the beam of light indicating that the cap is 'off'. The light transmitter(s) and light receiver(s) may be positioned on the base or sides of the adherence monitor or at any other position where they may detect movement of the cap 6, tether 7 or both the cap 6 and tether 7.

In an alternative embodiment, the light transmitter(s) may transmit a normal beam of light, which will generally disperse outwardly from the point of transmission. The movement of the cap 6 or the tether 7 will therefore affect the light signal, for example by the light reflecting off the cap 6 or tether 7 as they move. This will alter the intensity of light being received by the light receiver(s), thus enabling the sensor to register the movement of the cap. In such an embodiment, it may not be necessary that the cap or tether block the light signal to enable the position of the cap to be detected and/or counted. Hence, the light transmitter(s) and light receiver(s) need not necessarily be positioned substantially opposite each other. It is also possible that the light transmitter(s) and light receiver(s) could be positioned next to each other or side by side.

For most medicament inhalers with a cap, the attachment of the cap on to the mouthpiece results in an audible sound, such as a click, as a cap retaining feature engages with a complimentary retaining feature provided on the medicament inhaler. The disengagement of these retaining features may also provide a distinctive audible sound or vibration.

The adherence monitor 10 may include a cap detection system, as will be described below.

In other forms the adherence monitor 10 may monitor or detect whether the cap 6 is positioned on or off the mouthpiece 6 of the medicament inhaler 1 using an acoustic, vibration, audio, or pressure sensor to detect the replacement or removal of the cap 6. The acoustic, vibrational or audible features during removal and replacement of the medicament inhaler cap 6 with tether 7 may be characterised to facilitate detection of when the cap is 'on' versus when the cap is 'off'. An addressee of ordinary skill would understand that the acoustic, vibration, audio, or pressure sensor (not shown) may be positioned on or in the second housing 11 of the adherence monitor 10 in any location that allows detection of the sound, vibration or pressure resulting from movement of the cap 6 or tether 7.

Characterisation of the vibrational, audio or pressure differences between delivery of a dose of medicament when the cap is on or covering the mouthpiece 5 versus when the delivery of a dose of medicament when the cap is off or not covering the mouthpiece 5 may also be completed. Such characterisation may enable determination of the cap status during delivery of a dose of medicament to facilitate improved compliance monitoring by the adherence monitor 10.

In other forms the adherence monitor 10 may include a force sensor resistor, pressure switch or pressure sensor configured to detect the tension of the tether 7 to enable determination of when the cap is in the 'on' or 'off' status. The force sensor resistor or pressure sensor may be coupled to or in contact to at least a portion of the tether 7 to facilitate detection in a change in tension force or pressure. In some forms the sensor may be in the form a thin film or band configured to be positioned under or over at least a portion of the tether 7. The sensor may be co-moulded into or onto a portion of the second housing 11. In some forms a force sensor, pressure switch or pressure sensor may detect the displacement of the cap 6.

Figure 10:
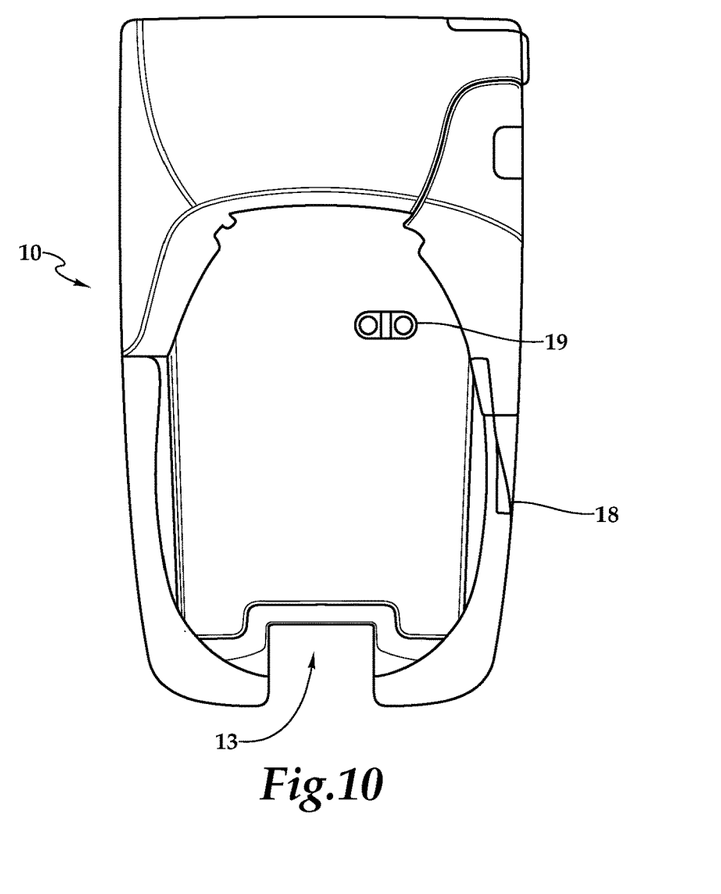
FIG. 10 is a front view of the embodiment illustrated in FIG. 2, without the inhaler and with the hinged door closed.

Referring to FIG. 10, the cap detection system may include a cap switch 18, located on the front edge of the second housing 11 which abuts the cap 6 when it is placed on the mouthpiece 5. The cap switch 18 is configured to enable detection of the cap 6 being placed on or over the mouthpiece 5. The switch 18 may be actuated (or de-actuated) by the cap 6 during the action of removing and replacing the cap 6 on the mouthpiece 5, following which an appropriate electrical signal is sent to an electronics control module (ECM). The switch may advantageously or preferably be an electronic or electromechanical switch, although any type of switch is within the scope of some embodiments.

The cap detection system may include a plurality of sensors configured to detect a range of parameters related to the removal and replacement of the cap 6 or tether 7. The plurality of sensors may include different types of sensors including one or more of the sensors referred to herein, e.g. acoustic, pressure, vibrational, optical and force pressure sensors. The ECM may collate the information received from the plurality of sensors to improve accuracy of the cap detection system.

In some forms the adherence monitor 10 may monitor or detect whether the cap 6 is 'on' or 'off' the mouthpiece 5 at the time of delivery of the dose of medicament. Alternatively, the adherence monitor 10 may continuously monitor or monitor on a regular basis the status of the cap 6.

The adherence monitor 10 may be configured to distinguish when a dose of medicament is delivered and the cap 6 is 'on' from when a dose of medicament is delivered and the cap 6 is 'off'. Thus, the adherence monitor 10 may monitor or detect and record when correct delivery of a dose of medicament has been delivered.

In some forms the adherence monitor 10 may be configured to provide an alert or alarm system to identify when the cap 6 has not been replaced on or over the mouthpiece 5 or has been off for a period of time. The alert or alarm may act as a reminder to the user to replace the cap to help impede or prevent soiling of the inhaler mouthpiece. The alert or alarm may be configured to provide a signal. The signal may be provided in one or more form such as an audible, visual or tactile form. For example, the signal may be a light, LED, audible signal, vibrational signal or the like. The signal may be provided directly on or by the adherence monitor 10 or may be sent to an electronically coupled device such as a mobile phone other form of mobile computing device or computer.

In some forms the alert or alarm may be configured to activate following detection of predetermined events. The predetermined events may include one or more of the detection of the cap being removed (detected cap 'off' status); detection of administration of a dose of medicament (correctly or incorrectly); reminder to take next dose of medication; or other similar events. For example, the alert or alarm may be configured to activate following expiry of a predetermined period of time after the predetermined event has occurred. The predetermined period of time may be between 1 second and 60 minutes, such as 5, 10, 20, 30, 40, 50, 60, 90, or 120 seconds; 1, 2, 3, 4, 5, 10, 20 or 30 minutes or at any other time similar time limit. The setting parameters for the alert or alarm may be configurable by the user. For example, the user may be able to select or set one or more of the predetermined period of time; the types of predetermined events, the type of alert of alarm or to turn off the alert or alarm.

The adherence monitor 10 includes an electronics control module (ECM or processor, not shown) which is included within either a side or the base of the second housing 11. The ECM is adapted to monitor and/or manipulate and/or store and/or transmit compliance data relating to patient usage of the inhaler 1. The electronic controls and sensors are distributed throughout the device. To allow for more ergonomic feel of the device, the PCB is angled in relation to the device, and this allows for a wider base of the device and narrow top. Flex-rigid PCB may be used to mount the ECM and sensors.

Because the second housing 11 is releasably attachable to the inhaler 1, it may be appreciated that the adherence monitor 10 may be portable and/or reusable across a range of different medicament inhalers.

The adherence monitor 10 may include a dose detection device in the form of a first electromechanical switch 14 (see FIG. 3), which is in electronic communication with the ECM. The switch 14 may be located on the inner surface of the top portion of the adherence monitor 1. The location of the switch 14 must or should be such that during the movement of the downward-directed surface 9 the edge of the surface 9 actuates the switch when the inhaler is fired and the dose of the medicament is dispensed.

When a dose of medicament is dispensed and the switch 14 is actuated, an appropriate signal is sent to the ECM, where the dispensing of the dose is recorded, and the date and time of the dispensing of the dose is also recorded. Such a dose detecting apparatus has been previously described in our patent application WO2013/043063, which is incorporated herein, in its entirety, by reference.

In some forms the adherence monitor 10 may include a dose detection device in a form of a switch or sensor located in or on the second housing 11 and configured to detect that the dose of the medicament is dispensed. The dose detection device may include one or more of an acoustic sensor, vibrational sensor, thermistor, pressure sensor, pressure switch, force sensor resistor, audible sensor, optical sensor or proximity sensor, mechanical switch. Depending on the type of switch or sensor selected, different signals may be used to detect a dose detection being dispensed: change in pressure, temperature, volume, visible or IR light intensity, etc.

Adherence monitor 10 as described includes an ECM, with the ECM being adapted to monitor and/or manipulate and/or store and/or transmit all adherence data gathered, relating to the patient usage of the medicament delivery device. The ECM may be a suitable microprocessor device.

The use of ECM's, in conjunction with adherence monitors for medicament delivery devices, are well known, and it is not intended therefore to describe them in any significant detail herein. For example, these systems are in general terms in commercial use in products available from the present applicant and related companies, as well as disclosed in the applicant's prior patent filings, for example those incorporated by reference herein. An example of an adherence monitor, used in conjunction with an ECM and/or transmitter can be found in our U.S. Pat. No. 8,424,517 and our US Patent Publication No. 2014/0000598, the contents of which are incorporated herein in their entirety.

The ECM is powered by a battery, and either a rechargeable or replaceable battery may be used. The ECM and/or the adherence monitor may alternatively be powered by any suitable alternative devices, for example a kinetic charger, or by solar power.

The ECM stores and transmits the adherence data gathered, so that analysis can determine if the user has used the inhaler correctly and/or incorrectly. The inhaler use logs generated in the adherence monitor are uploaded into smartphone application, a PC or a central communication hub, and through those into a web based server. In some embodiments, the inhaler use logs may also be uploaded from the adherence monitor directly into a web based server.

Adherence monitor 10 includes a memory. In some embodiments, a volatile type computer memory, including for example RAM, DRAM, SRAM, may be used. In such instances, the adherence monitor may continually transmit information to the computing device external to the adherence monitor or medicament delivery device. In other embodiments non-volatile memory formats may be used, including for example ROM, EEPROM, flash memory, ferroelectric RAM (F-RAM), optical and magnetic computer memory storage devices, and others.

As seen in FIG. 10, the adherence monitor 10 may also include a inhaler sensor 19 for detection whether monitor 10 is attached to inhaler 1. The inhaler sensor 19 may be an IR optical sensor or a proximity sensor. Any other suitable sensor may be used. In some forms the inhaler sensor 19 may be located in an internal surface of the second housing 11.

The adherence monitor 10 may also include indication devices, such as LED to indicate an event and/or to alert the user if the ECM determines that the user has used the inhaler correctly and/or incorrectly. The indication devices may be utilised to alert the user if they have attempted to dispense a dose of medicament with the cap 6 still attached. Alternatively, the indication devices may be used to alert if medication has not been dispensed within certain timeframe, e.g. every 12 h or 24 h.

The indication devices may be in the form of one or more LEDs, or in the form of some other visual and/or audio and/or vibrational indicator. Adherence monitor 10 also includes a multi-function user button for monitoring and controlling several aspects of operation. For example, pushing the button once may result in a green light showing if the adherence monitor 10 is fitted to the inhaler 1 correctly, and in normal working order. Conversely, a red light may indicate a problem. Pushing the button twice may provide for another aspect of the adherence monitor to be checked or reported, and furthermore pushing and holding the button may result in yet another function or check being done.

The adherence monitor 10 may also include a user interface (not shown) enabling the user to access data recorded or received by the adherence monitor and also change the settings of the adherence monitor (for example, date/time, visual/audio alert settings). The user interface may also be used to access any data received (or transmitted) by the adherence monitor or to control the upload of the data from the adherence monitor to an external electronic device. The user interface may be located in the exterior surface of the second housing 11.

The embodiments of the adherence monitor 10 and/or the ECM described herein may be able to monitor for any type of non-dose counting information relating to the operation of the inhaler 1, and/or patient usage of the inhaler 1. For example, the ECM may include a real-time clock (or be in electronic communication with one) to enable the adherence monitor 10 to record a date and time for each dose of medicament dispensed. The ECM may be calibrated to compare the actual doses dispensed against the table of pre-set dosage times and, if the dose is not dispensed at the pre-set time, alert the user that a dose is due.

Furthermore, and for example only, adherence monitor 10 and/or the ECM may also be able to monitor criteria such as geographical location, temperature, humidity, the orientation of the inhaler 1, the condition of the medicament, the amount of medicament left, the condition of the battery or whether it is installed, the flow or pressure of the user's inhalation, an audio sensor for detecting inhalation or for determining if the main body portion has been rotated with respect to the base portion, and so on. To this effect, the ECM may include an audio or optical inhalation sensor, thermistor sensor or accelerometer, or be connected to a GPS (e.g. the adherence data from the smartphone paired with the adherence monitor 10 may be matched with the GPS data relating to the location of adherence events received by the smartphone).

Adherence monitor 10 may also include a communication device for transmitting the adherence data. In one embodiment, this may be a USB port located on the second housing 11 of the adherence monitor 10. Any other suitable wired connections or ports may be used.

Alternatively and/or additionally, the adherence monitor 10 and/or ECM may be provided with a wireless transmitter and/or a wireless transceiver e.g. Bluetooth Low Energy™ module to be able to transmit and/or receive data respectively. Any other suitable wireless technology known in the art may be used, including for example Wi-Fi (IEEE 802.11), Bluetooth™, other radio frequencies, Infra-Red (IR), GSM, CDMA, GPRS, 3G, 4G, W-CDMA, EDGE or DCDMA200 or similar.

The data may be transmitted to a remote computer server or to an adjacent electronic device such as a smart phone or electronic tablet. The adherence monitor may be paired with a smartphone loaded with a software application which allows the smartphone to access, process, and/or present the data collected by the adherence monitor. The smartphone may be configured to transfer the data obtained from the adherence monitor to a web services platform. The data may be transmitted in real time, manually or at predetermined set times.

While the embodiments described above are currently advantageous or preferred, it will be appreciated that a wide range of other variations might also be made within the general spirit and scope of some embodiments.

For example, other types of switches may be used to detect the absence or presence of the tethered cap on the mouthpiece of the inhaler: e.g. any type of carbon pill, tack switch or detector switch may be used. Some examples of suitable switches include: http://www.digikev.co.nz/product-detail/en/ESE-13V01D/P13356SCT-ND/822292; http://www.digikev.co.nz/product-detail/en/ESE-16J001/P14266SCT-ND/2193025; or http://www.digikey.co.nz/product-detail/en/FSM4JSMATR/450-1759-1-ND/2271638.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

All patent and other references noted in the specification, including websites, are hereby incorporated by reference.

The invention claimed is:

1. An adherence monitor for a medicament inhaler, the inhaler including a body, a mouthpiece for operatively inhaling a medicament, a cap for the mouthpiece, and a tether connecting the cap to the body, the adherence monitor comprising:
    a housing configured to enclose at least a portion of the body of the medicament inhaler in use, and
    a tether opening formed in the housing, the tether opening configured to receive the tether, the adherence monitor being configured to be fitted to the inhaler in a position at least partially surrounding the body of the inhaler without removing the cap from the tether and without removing the cap from the mouthpiece and a path length of the tether around the adherence monitor is unchanged relative to the path length of the tether when the adherence monitor is not fitted to the inhaler, such that cap and tether function of the medicament inhaler avoids being modified by placement of the medicament inhaler into the adherence monitor;
    wherein the tether opening is a slot extending through a base portion of the housing;
    wherein the tether operatively passes through the slot, around the base portion to the mouthpiece;
    wherein the housing includes an opening at a front thereof, the opening being between an interior of the housing where the body of the inhaler is located and an exterior of the housing;
    the opening having a lateral border between sides of the housing and the opening, the lateral border having a lower portion extending further forward than a recessed portion of the lateral border above the lower portion;
    said base portion including a left floor portion and a right floor portion;
    said floor portions located on opposite sides of said tether opening;
    said floor portions sized and oriented to support a lower end of the body of the medicament inhaler and prevent downward movement relative to the adherence monitor;
    said floor portions bounded by a rear wall extending upwardly from rearward portions of said floor;
    said rear wall resisting rearward movement of the medicament inhaler relative to said floor of said base portion;
    said floor portions bounded by side walls extending upwardly from lateral portions of said floor opposite said tether slot and extending up to transition into becoming said sides of the housing;
    said side walls resisting lateral movement of the medicament inhaler relative to said floor of said base portion;
    said floor portions bounded by front walls extending upwardly at least partially from forward portions of said floor;
    said front walls resisting forward movement of said medicament inhaler relative to said floor of said base portion;
    said floor portions bounded on inner sides thereof closest to each other by said slot of said tether opening;
    said rear wall, said lateral walls and said front walls acting together to keep the medicament inhaler restrained, when inserted into the adherence monitor and in contact with the floor, from any motion other than vertical motion of a canister of the medicament inhaler relative to an actuator of the medicament inhaler for dispensing of a dose of medicament out of the canister and through the mouthpiece;
    wherein portions of said front walls above said floor portions terminate below the cap of the medicament inhaler when the cap is located upon the mouthpiece of the medicament inhaler and the medicament inhaler is located adjacent to said floor portions, such that transitioning of said cap from being on said mouthpiece and off of said mouthpiece occurs freely and fully without interference by said front walls extending upwardly at least partially from forward portions of said floor portions;
    wherein said opening in said front of the adherence monitor and said lateral border of said opening of the adherence monitor are positioned to avoid blocking a downward-directed surface coupled to the canister of the medicament inhaler and located on a front side of the medicament inhaler, such that the medicament inhaler is free from obstruction by the adherence monitor, whether the downward-directed surface is in a first position or a second position that is moved downward relative to the first position when the cap of the medicament inhaler is off of the mouthpiece for actuation of the medicament inhaler; and said opening allowing the cap of the medicament inhaler to be placed on the mouthpiece of the medicament inhaler and block downward movement of the downward-directed surface and actuation of the medicament inhaler without interference by the adherence monitor.

2. The adherence monitor according to claim 1, wherein the tether opening is formed and positioned such that the tether is removable from the tether opening whilst the adherence monitor is operatively engaged with the inhaler.

3. The adherence monitor according to claim 1, wherein the housing includes at least one retainer configured to engage with a base portion of a medicament inhaler when the medicament inhaler is received within the housing.

4. The adherence monitor according to claim 1, further including a cap sensor configured to detect a position of at least one of the cap or the tether of the inhaler when the inhaler is received within the adherence monitor.

5. The adherence monitor according to claim 4, wherein the cap sensor is configured to detect a cap on status, the cap on status being when the cap of the inhaler is positioned on or over the mouthpiece of the inhaler.

6. The adherence monitor according to claim 4, wherein the cap sensor is configured to detect a cap off status, the cap off status being when the cap of the inhaler has been removed from or is not covering the mouthpiece of the inhaler.

7. The adherence monitor according to claim 4, further including an alert signal sent to a user following detection of a predetermined event.

8. The adherence monitor according to claim 7, wherein the predetermined event includes one or more of (i) the cap is removed from the mouthpiece of the inhaler; (ii) a dose of medicament has been administered (iii) time to take next dose of medication.

9. The adherence monitor according to claim 7, wherein the alert signal is sent following expiry of a predetermined period of time following detection of the predetermined event.

10. The adherence monitor according to claim 9, wherein the predetermined period of time is greater than 1 second and less than 60 minutes.

11. The adherence monitor according to claim 9, wherein the predetermined period of time is set by a user.

12. The adherence monitor according to claim 7, wherein the predetermined event is detection of when the cap has been removed for a predetermined period of time.

13. The adherence monitor according to claim 12, wherein the predetermined period of time is between 5 seconds and 30 minutes.

14. The adherence monitor according to claim 1, wherein a cap sensor includes at least one sensor configured to detect a status of at least one of the cap or the tether of the inhaler.

15. The adherence monitor according to claim 14, wherein the at least one sensor includes at least one of an acoustic sensor, vibrational sensor, pressure sensor, pressure switch, force sensor resistor, audible sensor, optical sensor or proximity sensor.

16. The adherence monitor according to claim 1, wherein the inhaler includes a movable dose counter housing that moves when a dose of medicament is dispensed by the inhaler, the adherence monitor further including a dose detection switch, wherein the dose detection switch is configured to be operatively actuated by the movement of the dose counter housing.

17. The adherence monitor according to claim 1, wherein the recessed portion of the lateral border has a curvature matching a cap lateral edge curvature.

18. The adherence monitor according to claim 1, wherein the recessed portion of the lateral border is recessed rearwardly at least as much as a cap lateral edge contour.

19. The adherence monitor according to claim 1, wherein the opening is sized to avoid interference with the cap on the mouthpiece of the medicament inhaler.

20. A method for fitting an adherence monitor according to claim 1 to a medicament inhaler, the medicament inhaler including a body, a mouthpiece for operatively inhaling the medicament, a cap for the mouthpiece, and a tether connecting the cap to the body, the method including the steps of:

placing the medicament inhaler through an opening in the front of the housing of the adherence monitor, the adherence monitor including the housing configured to enclose at least a portion of the medicament inhaler in use, the tether opening configured to receive the tether, the adherence monitor being configured to be fitted to the inhaler without removing the cap from the tether and without removing the cap from the mouthpiece and the path length of the tether around the monitor is unchanged relative to the path length of the tether when the adherence monitor is not added to the inhaler, and wherein the tether operatively passes through the slot, around the base to the mouthpiece;

keeping the cap on the mouthpiece during said placing step with the opening in the front of the housing avoiding interference with the cap located upon the mouthpiece and the slot avoiding interference with the tether;

removing the cap from the mouthpiece when the inhaler is to be used, without cap removal being interfered with by the adherence monitor; and replacing the cap upon the mouthpiece after the inhaler has been used, without cap replacement being interfered with by the adherence monitor.

\* \* \* \* \*